(12) United States Patent
Brandl et al.

(10) Patent No.: US 6,399,094 B1
(45) Date of Patent: *Jun. 4, 2002

(54) UNILAMELLAR LIPOSOMAL PREPARATIONS WITH HIGH ACTIVE SUBSTANCE CONTENT

(75) Inventors: Martin Brandl, Rötebuckweg 9, 79104 Freiburg; Dieter Bachmann, Hamburg; Regine Reszka, Schwanebeck; Markus Drechsler, Berlin, all of (DE)

(73) Assignees: Martin Brandl; Max-Delbrück-Centrum für Molekulare Medizin, both of (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/803,435

(22) Filed: Feb. 20, 1997

Related U.S. Application Data

(63) Continuation-in-part of application No. PCT/DE95/01162, filed on Aug. 18, 1995.

(51) Int. Cl.[7] .......................... A61K 9/127; A61K 9/133
(52) U.S. Cl. ..................... 424/450; 428/402.2; 264/4.1; 264/4.3
(58) Field of Search ................................. 424/450, 1.21, 424/9.321, 9.51, 417, 94.3, 812; 428/402.2; 264/4.1, 4.3; 436/829; 935/54

(56) References Cited

U.S. PATENT DOCUMENTS

| | | | |
|---|---|---|---|
| 4,877,561 A | 10/1989 | Iga et al. | |
| 5,376,183 A | * 12/1994 | Galt | .............................. 134/40 |
| 5,498,420 A | * 3/1996 | Edger | .......................... 424/450 |
| 5,527,538 A | 6/1996 | Baldeschwieler | |

FOREIGN PATENT DOCUMENTS

| | | | |
|---|---|---|---|
| DE | 4341472 | | 6/1995 |
| EP | 00 69307 | * | 1/1983 |
| EP | 0087993 | * | 9/1983 |
| EP | 0240346 | | 10/1987 |
| EP | 00509338 | | 10/1992 |
| EP | 0565361 | | 10/1993 |
| EP | 0661044 | | 7/1995 |
| EP | 0697214 | | 2/1996 |
| EP | 0719546 | | 7/1996 |
| GB | 2002319 | * | 2/1979 |
| WO | 9640061 | | 12/1996 |
| WO | 9640064 | | 12/1996 |

OTHER PUBLICATIONS

Brandl. in Liposome Technology vol. 1, p. 50–64, 1993.*
Ghyczy in Seifer–Ole–Fe–He–Wachse 117 Jg N& 10, 1991.*
Pick Archives of Biochem & Biophys 212 #1 p. 186–194, 1981.*
Gregoriadis in Liposome Tech. vol. 1 p. 37, 1993.*
Cheng in Investigative Radiology vol. 22 #1 p. 47, 1987.*

(List continued on next page.)

Primary Examiner—Gollamudi S. Kishore
(74) Attorney, Agent, or Firm—Norris, McLaughlin & Marcus

(57) ABSTRACT

A liposomal vesicular preparation with good encapsulation efficiency for active ingredients, based on homogeneous unilamellar liposomal vesicular lipids, has a substantially tightly packed vesicular structure and forms carriers of active ingredients. At least 20% by weight relative to the total weight of the liposomal vesicular preparation of the active ingredient (drug substances, vaccines, diagnostics, vectors) are present in encapsulated form inside the homogeneous unilamellar liposomal vesicular lipids. The liposomal vesicular preparation is a semi-solid liposomal vesicular lipid gel. The membrane forming amphiphiles can be members of from the group consisting of lipids, phospholipids and synthetic amphiphiles.

6 Claims, 5 Drawing Sheets

OTHER PUBLICATIONS

"Techniques for Encapsulating Bioactive Agents Into Liposomes", by Lawrence D. Mayer et al., In Chemistry and Physics of Lipids, Jun./ Jul. 1996, vol. 40, No. 2—4, pp. 87—88 and 333—345, Elsevier Scientific Ireland Ltd.

"Liposome Preparation using High–pressure Homogenizers", in G. Gregoriadis (Ed.) Liposome Technology 2nd edition, 1993, vol. 1, pp. 49–65, CRC, Boca Raton by M. Brandl aet al.

"Unilamellar liposomes made with the French pressure cell: a simple preparative and semiquantitative technique", by Hamilton et al., published in Journal of Lipid Research, vol. 21, 1980, pp. 981–992.

* cited by examiner (-□-) total, (-○-) free, (-△-) liposomal calcein.

UNILAMELLAR LIPOSOMAL PREPARATIONS WITH HIGH ACTIVE SUBSTANCE CONTENT

CROSS-REFERENCE TO RELATED APPLICATION

This application is a continuation-in-part application of another international application filed under the Patent Cooperation Treaty on Aug. 18, 1995, bearing Application No. PCT/DE95/01162, and listing the United States as a designated and/or elected country. The entire disclosure of this latter application, including the drawings thereof, is hereby incorporated in this application as if fully set forth herein.

BACKGROUND OF THE INVENTION

1. Field of the Invention

The present invention relates to a liposomal preparation, its production and use. Areas of application are pharmacy and medicine, particularly its use as carrier systems for drug substances, vaccines, diagnostics and vectors.

2. Brief Description of the Background of the Invention Including Prior Art

Liposomes have gained increasing importance in the past years as carriers or encapsulation means for various substances, particularly in medical applications (see Liposomes from Physics to Applications, D. D. Lasic, Elsevier, Amsterdam 1993). Among the various types of liposomes mostly those are regarded favorable, which have a small to intermediate vesicle size such as from about 10 to 300 nm with good size uniformity and which have one single membrane shell and provide a unilamellar vesicle. Moreover, the active substances should be entrapped or incorporated in the liposomes in an efficient manner.

For the preparation of liposomes, numerous methods have been described. These methods, however, fulfill only insufficiently at least one of the above mentioned main requirements—small to intermediate liposome size or high encapsulation efficiency. This is mainly the case when the active substance is water soluble and thus should be encapsulated and entrapped in the aqueous interior of the liposomes. The so-called DRV-method and the so-called REV-method both yield good encapsulation efficiencies but at the same time yield populations of inhomogeneous, mostly large liposomes. In contrast, other previously reported preparation methods based on ultrasonic treatment, high-pressure homogenization or detergent removal and dialysis can achieve in case of homogeneous, small to intermediate sized liposomes only a poor encapsulation efficiency, particularly with water soluble substances (Liposome Technology 2nd edition, volume I–III, G. Gregoriadis (Ed.), CRC Press Inc., Boca Raton, Flo., 1993, 37–48; D. Bachmann et al. Preparation of Liposomes using a Mini-Lab 8.30 H high-pressure homogenizer, Int. J. Pharm. 91, 1/93, 69–74).

Liposomes, after three decades of research, are still gaining increasing interest with special emphasis more recently on their use as drug carrier systems. For therapeutic purposes, they must be loaded with active substances. This is more easily achieved with lipophilic or amphiphilic molecules as they have a tendency to be incorporated in the liposomal membrane. In contrast, hydrophilic molecules must be encapsulated in the aqueous interior which, in general, cannot easily be performed in an efficient manner.

A variety of liposome preparation techniques have been developed over the past three decades, none of them, however, perfectly fulfilling the two basic requirements homogeneous and not too large liposome sizes and efficient encapsulation of hydrophilic molecules at the same time. Whereas the dehydration-rehydration vesicles DRV techniques (C. Kirby and G. Gregoriadis, 1984, Dehydration-rehydration vesicles: a simple method for high yield drug entrapment in liposomes, Biotechnology, pp. 979–984), and reverse-space evaporation techniques REV (F. Szoka and D. Papahadjopoulos, 1978, Procedure for preparation of liposomes with large internal aqueous space and high capture by reverse-phase evaporation, Proc. Natl. Acad. Sci., USA 75, 4194–4198), achieve high encapsulation efficiencies but only relatively large and heterogeneous liposome sizes, it is just the opposite with high-pressure homogenization (M. Brandl, D. Bachmann, M. Drechsler, and K. H. Bauer, 1990, Liposome preparation by a new high-pressure homogenizer Gavlin Macron Lab 40 Drug Dev. Ind. Pharm. 16, 2167–2192; M. Brandl, D. Bachmann, M. Drechsler, and K. H. Bauer, 1993, Liposome Preparation using High-pressure Homogenizers, in G. Gregoriadis (Ed.) Liposome Technology 2nd edition, Vol. 1, pp. 49–65, CRC, Boca Raton), or detergent depletion techniques (J. Brunner, P. Skrabal, and H. Hauser, 1976, Single bilayer vesicles prepared without sonication, physico-chemical properties, Biochim. Biophys. Acta 455, 322–331). The concept at the beginning of the invention was fairly straightforward: for low-molecular weight hydrophilic molecules, which represent the majority of classical drug substances, the degree of entrapment into liposomes can be regarded a result of partition of the aqueous drug solution at the moment of liposome formation into a compartment inside the liposomes and a compartment in-between the liposomes.

The ratio of volume inside the liposomes compared to the total aqueous volume of the preparation is defined as encapsulation efficiency. The ratio can theoretically be increased by two alterations within the system: Firstly, when at constant lipid concentration, only a few large liposomes are formed instead of many small liposomes, the entrapped aqueous volume is increased. For technical, and in the case of i.v. injection, also for pharmacokinetic reasons, the enlargement of liposome size is confined to narrow limits. In the case of i.v. injection liposomes sizes between 70 and not more than 200 (D. Liu, A. Mori, and L. Huang, 1992, Role of liposome size and res. blockade in controlling biodistribution and tumor uptake of gml-containing liposomes, Biochem. Biophys. Acta 1104, 95–101), and sufficient size homogeneity (D. Liu and L. Huang, 1992, Size homogeneity of a liposome preparation is crucial for liposome biodistribution in vivo, J. Liposome Res. 2, 57–66), are regarded as favorable for most applications. Secondly, with increasing lipid concentration, more liposomes per unit volume of the preparation are formed. This again should lead to an increase in the ratio of aqueous space inside compared to in-between the liposomes as long as liposome shape and lamellarity are unchanged. Phospholipid, however, when dispersed in aqueous medium at or above lipid contents of 200 to 300 mM result in highly viscous dispersions up to semisolid consistency. Although it was expected that these viscous to semi-solid preparations would no longer be liposome dispersions, it was of interest to prepare such "pastes" preferentially with homogeneous physicochemical characteristics. Based on previous experience with liposome preparation by the one-step technique (M. Brandl, D. Bachmann, M. Drechsler, and K. R. Bauer, 1990, Liposome preparation by a new high-pressure homogenizer Gavlin Macron Lab 40 Drug Dev. Ind. Pharm. 16, 2167–2192, M. Brandl, D. Bachmann, M. Drechsler, and K. H. Bauer, 1993, Liposome Preparation using High-pressure Homogenizers, in G. Gregoriadis (Ed.) Liposome Technology 2nd edition, Vol. 1, pp. 49–65, CRC, Boca Raton), high-pressure homogenization for "forced hydration" of lipids was employed.

In order to study the inner structure of the pastes in terms of homogeneity, freeze fracture electron microscopical visualization was used. It was noticed that these pastes may retain hydrophilic markers and thus potentially serve as depot formulations for controlled release of drugs. The drug release behavior of the pastes was further analyzed in a standard in-vitro continuous flow through apparatus as normally employed for release tests of ointments. Preliminary reports of this project have been published recently, M. Brandl and R. Reszka, 1995, Preparation and characterization of phospholipid membrane gels as depot formulations for potential use as implants, Proc. Intern. Symp. Control. Rel. Bioac. Mater. 22, 472–473; M. Brandl, C. Tardi, M. Menzel, and R. Reszka, 1995, Highly concentrated phospholipid dispersions: preparation by high pressure homogenization and analysis of drug release. Proceedings 4th Liposome Res. Days. Freiburg PSI (not completely legible in publication); M. Brandl, D. Bachmann, R. Reszka, and M. Drechsler, 1996, Unilamellar Liposomal Preparations with High Active Substance Content.

SUMMARY OF THE INVENTION

1. Purposes of the Invention

The goal of the invention is to make a liposomal preparation with good encapsulation efficiency for active substances, based on homogeneous liposomes of small to intermediate size.

These and other objects and advantages of the present invention will become evident from the description which follows.

2. Brief Description of the Invention

The present invention provides a liposomal preparation comprising homogeneous unilamellar liposomes of small to intermediate size, having a vesicular structure in tight packing, and forming carriers of active substances, and at least 20% by weight relative to the total weight of the liposomal preparation of an active ingredient in entrapped form inside the homogeneous unilamellar liposomes, wherein the liposome preparation forms a highly viscous liposome gel.

The liposomal preparation preferably contains more than 95 percent by weight of the homogeneous unilamellar liposomes exhibiting a diameter of from about 10 to 300 nm, and has the active substances as members selected from the group consisting of drug substances, vaccines, diagnostics, vectors, and mixtures thereof.

According to the invention a liposomal preparation is produced comprising the steps of subjecting a mixture comprising membrane-forming amphiphiles, solvent and an active ingredient, which active ingredient is to be encapsulated, to a high-pressure homogenization under pressures of from about 50 to 1600 bar (5–160 MPa), subsequently removing the solvent, subsequently freezing the mixture, thawing the mixture, and transferring the mixture into a freely flowing dispersion. Furthermore a step of extruding the mixture through filters having a pore width of from about 0.1 to 1 $\mu$m can follow.

Preferably the solvent employed is removed by evaporation or by spray drying. The subjecting to the high-pressure homogenization can be preceded by a preparation of a thin, dry lipid film of the membrane-forming amphiphiles. The solvent is preferably water. Advantageously, the mixture is subjected at least two times and not more than 50 times to the high-pressure homogenization.

The membrane-forming amphiphiles can be members selected from the group consisting of lipids, phospholipids of natural orogin, phospholipids of synthetic origin, synthetic amphiphiles, and mixtures thereof. The lipid can be cholesterol. The phospholipid can be a member selected from the group consisting of phosphatidyl choline, phosphatidyl glycerol and mixtures thereof. The synthetic amphiphiles can be reactants of members selected from the group consisting of block-copolymers, alkyl esters, alkyl ethers and alkyl amides and mixtures thereof formed with members selected from the group consisting of alcohols, diols, triols, polyols, amines, amino acids, peptides, saccharides and mixtures thereof.

A liposomal preparation can be applied, which comprises homogeneous unilamellar liposomes of small to intermediate size, having a vesicular structure in tight packing, and forming carriers of active substances; and at least 20% by weight relative to the total weight of the liposomal preparation of an active ingredient in entrapped form inside the homogeneous unilamellar liposomes, wherein the liposome preparation forms a highly viscous liposome gel, for effecting a release of liposomes in aqueous medium under retention of a high proportion of the active ingredient present in entrapped form. At least 20% of the active ingredient can be present in entrapped form.

The invention furnishes further a liposomal preparation, consisting of liposomes as carriers of active substances such as drug substances, vaccines, diagnostics, as well as vectors, characterized in that it consists of homogeneous unilamellar liposomes of small to intermediate size, preferably having a diameter of 10 to 300 nm, having a vesicular structure in tight packing, and it contains at least 20% of the active ingredient in entrapped form and represents a highly viscous liposome gel.

A mixture of membrane-forming amphiphiles, water and active ingredient is to be encapsulated and is subjected one time or several times, at the most fifty times, to a high-pressure homogenization with pressures of from 50 to 1600 bar (5–160 MPa), if necessary after preparation of a thin, dry lipid film and subsequent removal of the solvent by evaporation or spray drying, and wherein there occurs subsequently, if necessary, a treatment by freezing and thawing, and, if suitable, a transfer into a freely flowing dispersion and subsequently, if suitable, an extrusion through filters having a pore size of 0.1 to 1 $\mu$m. Lipids, phospholipids of natural or synthetic origin or synthetic amphiphiles are employed as membrane-forming amphiphiles. Preferably cholesterol is employed as lipid. Preferably, phosphatidyl choline or phosphatidyl glycerol is employed as phospholipid. Block-copolymers, alkyl esters, alkyl ethers and alkyl amides of alcohols, diols, triols and polyols, amines, amino acids, peptides, and saccharides can be employed as synthetic amphiphiles. The liposomal preparation can be applied for release of liposomes in aqueous medium under retention of a high proportion, preferably at least 20%, of the active ingredient in entrapped form.

The preparation of highly concentrated dispersions of phosphatidyl choline PC via high-pressure homogenization was described above. The obtained semi-solid matrices retained incorporated hydrophilic markers for time periods of at least several hours and thus appeared suitable as depot formulations for drugs. During in-vitro release tests, markers were found to be released in free as well as in liposome-entrapped form (compare M. Brandl, C. Tardi, M. Menzel, R. Reszka, Proc. 4th Lipos. Res. D., 1995).

Applicants investigated whether the release kinetics of the incorporated marker can be influenced by the concentration of phosphatidyl choline PC in the matrix. Applicants found that the overall tendency was a decrease of release rate with increasing lipid concentration for lipid concentrations between 30% and 60% (m/m). When comparing lipid concentrations of 40% and 50% (m/m), however, a dramatic change was found. Whereas 40% (m/m) matrices showed mean release rates of about 15% of total incorporated marker per hour and durations of about 6 hours until 100% release was achieved, the 50% (m/m) matrices released only 2% per hour in mean and release continued for more than 48 hours. The fraction of the marker released in liposome-entrapped form was also much smaller with the more concentrated matrix. None of the matrix was left in the release cell after the end of marker release from the 40% (m/m) preparation. In contrast with 50% (m/m) matrices, the cell still contained a remainder of the lipid matrix, which had been depleted of all marker.

These results indicate that structural changes of the matrices occur at a critical lipid concentration of from about 30% to 60%, and preferably from 40% and 50% (m/m). This observation agrees with results of freeze-fracture electron microscopical examination of the fine structure of the matrices. Matrices consisting of 40% or less of lipid showed structures of densely packed small unilamellar vesicles (SUVs) throughout. In contrast, matrices of lipid concentrations of 50% and above showed various structural elements besides SUVs, large multilamellar vesicles and planar staples of bilayers were also found. It is conceivable now that the described three-dimensional liposomal networks below the critical concentration solely consist of SUVs and thus fully erode by continuous "budding off" of intact liposomes. Above this critical concentration on the other hand, only a proportion of SUVs is embedded in less defined structures which do not erode easily. The marker in this case is released substantially exclusively via diffusion. In conclusion, raising the lipid concentration does not only affect the release rate but beyond a certain limit also causes a change in release mechanism.

Furthermore, highly concentrated, semi-solid phospholipid dispersions have been investigated. Their preparation is based on "forced hydration" of (phospho-)lipid(s) by high pressure homogenization in the presence of relatively low amounts of water. The inner structure of the obtained semisolid pastes, as revealed by freeze-fracture electron microscopy, can be best described as a matrix of densely packed vesicles. Depending on the lipid content, the characteristics of these vesicles range from very homogeneous, small and unilamellar to more heterogeneous in size as well as lamellarity. Although not comparable to "classical" liposome dispersions, these multivesicular pastes may be useful as drug carriers. Results from in-vitro release tests demonstrate that they may serve as local depots for controlled release of active compounds. Two release mechanisms are observed occurring at the same time: (1) release of free active molecules via diffusion out of the matrix and (2) budding off of active compound-carrying liposomes from the matrix. Release type and rate are determined among other factors by the phospholipid content of the matrices and thus by their inner structure.

Figure 1:
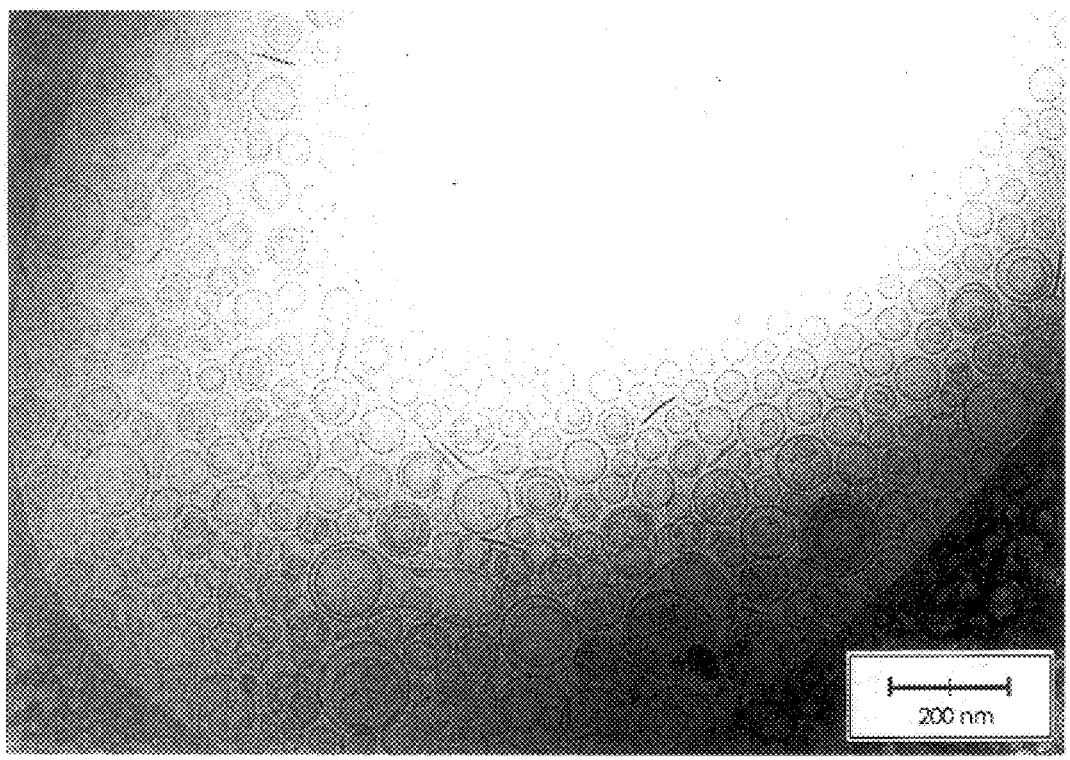
FIG. 1 is a view of a micrograph picture made by Cryo-electron microscopy of the liposomes as obtained after transfer of the preparation into a freely flowing liposome dispersion.

The novel features which are considered as characteristic for the invention are set forth in the appended claims. The invention itself, however, both as to its method of operation, its products and physical requirements, together with additional objects and advantages thereof, will be best understood from the following description of specific embodiments and examples.

DESCRIPTION OF INVENTION AND PREFERRED EMBODIMENT

The invention liposomal preparation consists of homogeneous small to intermediate sized, mostly unilamellar liposomes having a size of from 10 to 300 nm in diameter. The preparation is of a vesicular structure in tight packing and contains a high percentage, at least 20%, and in some cases up to 90%, of the active substance in liposomally entrapped form. The active substance includes a medically effective substance (medicinal substances), especially cytostatics, antibiotics, peptides and proteins; as well as substances or diagnostics which are applied onto or into the body for recognition and analytical determination of its function or state as well as the state or function of its tissues or organs; furthermore, it includes substances which exhibit an immunogenic effect (vaccines); furthermore, it includes substances which transfer genetic information and material within the framework of a gene therapy (vector). Only small portions of the active substance are present in free, i.e. non-liposomal form.

The appearance of the preparation is a highly viscous fluid or gel or a nearly clear to opalescent or slightly turbid gel. It contains besides (phospho-)lipids or other suitable amphipile membrane-forming substances, also medicinal substances, diagnostics, vaccines or also electrolytes, such as, for example, those useful for setting a specific osmotic pressure or a specific pH-value. The lipids used are for example cholesterol and its analogues, phospholipids of natural, semi-synthetic or synthetic origin, such as, for example, phosphatidyl choline, phosphatidyl glycerol and their analogues. Other membrane-forming amphiphiles are synthetic amphiphiles, for example, block-copolymers, alkyl esters, alkyl ethers, alkyl amides of alcohols, diols, triols and polyols, amines, amino acids, peptides or saccharides. The liposomes are so tightly packed that they form only a very small space remaining in-between the vesicles, but without affecting the vesicular structure. This structure has been called vesicular or liposome gel.

The vesicular or liposome gel can be stored at room temperature after the preparation and before dilution.

Because the achieved relative encapsulations in the preformed vesicles are relatively high, a removal and separation of unentrapped material can be avoided and dispensed with at least for certain applications. Therefore, there results in the obtained liposome gel a sufficiently high concentration of dissolved active substance within as well as surrounding the liposomes such that a leaking out of entrapped active substance from the vesicles or liposomes is not taking place. Since the vesicles or liposomes are within a three-dimensional assembly, they exhibit moreover a good storage stability in terms of vesicle size and lamellarity. This is probably due to the reduced mobility. i.e. due to the reduced kinetic energy of the bound liposomes which makes it less probable that the required kinetic impact energy for the aggregation and fusion of the liposomes is less easily reached. In cases where the liposome preparation undergoes freeze-thaw cycles during production, it appears favorable to store the preparation after the preceding freeze procedure at deep freezer temperatures and to thaw the preparation shortly before use.

The claimed liposomal preparation has three major advantages over preparations so far known:

Uptake of a proportion of the active ingredient which is up to 20-fold of what usually is achieved in small to medium-size unilamellar liposomes (an encapsulation or entrapment efficiency of 20 up to 90% as compared to usually 1 to 5%).

Good stability, which allows storage of at least three years before use.

Good size uniformity of the liposomes, wherein deviations are such that than 95% of the liposomes or vesicles have a typical diameter with a range of 100 nm.

The preparations are suitable as a direct depot of the entrapped active ingredient, for example, the preparations can be injected or, respectively, implanted.

Alternatively, the preformed liposomes or the liposomes from these preparations can be set free by stepwise addition of aqueous medium, possibly accompanied by mixing under low mechanical stress conditions, for example, by shaking or stirring, where said liposomes show unaltered small to intermediate sizes and only few (preferably just one) concentric lamellae, and where said liposomes contain unaltered a high percentage of active substance in entrapped form.

Aqueous medium mainly comprises purified water, according to the German Pharmacopoeia "In case of preparations for the parenteral application", "Water for Injection Purposes" according to the German Pharmacopoeia, which may contain dissolved inorganic or organic salts, acids or bases, for example, for setting and achieving a specific pH value or a specific osmotic pressure. However, the aqueous medium may also comprise aqueous solutions of saccharides, amino acids or mixtures of water with other solvents like alcohols, diols or triols. Suitable is for example a 0.9% sodium chloride solution or a 40 mmolar phosphate-buffer pH 7.4. Also these preparations of the most varied degree of dilution of the vesicular or liposome gel up to the freely flowing dispersion, are the object of this invention.

The invention production method for the preferred preparations according to the invention comprises the following steps:

1. Crude Mixture

Mixture of lipid(s), water, and active ingredients to be included (if required transferred into a crude dispersion and well dispersed by mixing with a magnetic stirrer or similar device).

2. Lipid Film

Alternatively, preparation of a lipid film can be produced and transferred into a crude mixture consisting of (phospho) lipid(s) and aqueous medium. The mentioned thin and dry lipid film is obtained by dissolution of the lipid(s) in organic solvents, which may also contain substances to be incorporated, and a subsequent removal of the solvent by evaporation or spray drying. Upon addition of aqueous medium, which may contain substances to be encapsulated, the lipid film is dispersed by shaking, stirring, kneading or other techniques. In this case, the temperature is increased if necessary to about 10° C. above the phase transition temperature of the phospholipids.

3. High-pressure Homogenization

The crude mixture obtained in steps 1 or 2 undergoes one or more (but not more than 50) cycles of the high-pressure homogenization at pressures between 50 and 1600 bar (corresponding to 5 to 160 MPa). If required, the crude mixture or educt, the homogenizer, and the final product are kept at elevated temperature and are possibly tempered.

4. Facultative Freeze/thaw Treatment

Based on one single freezing or a repeated freezing with subsequent thawing of the preparation during, i.e. between the individual cycles of the high-pressure homogenization or at the end thereof, a more homogeneous mixing of the preparation is achieved and the preformed liposomes may temporarily be destabilized such that liposomes with even more encapsulated substance can be formed.

5. Facultative Transfer into Freely Flowing Liposome dispersion

Based on a stepwise addition of aqueous medium in portions of 1 to 30% of the volume of the preparation and mechanical agitation and mixing by shaking or stirring, the three-dimensional gel framework is dispersed and the preformed liposomes are set free.

6. Facultative Limitation of the Maximum Liposome Size and Separation of Unentrapped Active Substance For certain applications, it is appropriate to separate or, respectively to comminute possibly individually appearing bigger liposomes or lipid aggregates by filtration (or extruding) of the preparation through membrane filters of pore sizes between 0.1 and 1 μm. In addition, germs can be removed by membrane filtration and thus a sterile preparation can be obtained. An excess of active substance, which was not entrapped in liposomes during the preparation, may be separated from these by size exclusion or gel permeation chromatography, dialysis, ultrafiltration, or ultracentrifugation techniques.

The invention preparation, which contains vesicles or liposomes in tight packing (vesicular or liposome gel) is suitable as an active substance depot, which is slowly releasing the incorporated active substance either in free and dissolved form or in the form of individual active substance-carrying vesicles or liposomes. This preparation can be applied by injection (for example, s.c., i.m., i.p.) or implantation. It is also possible to place it into body cavities or to apply it topically onto mucosa, the cornea of the eye (cornea), or parts of the skin. The preparation thus serves as a carrier of the active substance and is responsible for the modified or controlled release of the active substance.

Upon transfer into a freely flowing liposome dispersion it is suitable as carrier for active substances. This preparation can be applied by injection (for example i.v., i.m.) or by implantation. It is also possible to apply it into body cavities or topically to the skin (mucosa, cornea of the eye (cornea) or to parts of the skin). The entrapping liposomes lead to a distribution of the active substance carried by the liposomes in the body, which distribution selectively effects a high and long lasting concentration of the active substance at the site of action and thus to an improvement of the effect or to an improvement of the ratio of effect and side effect, or of the therapeutic index.

The invention will be explained in more detail in the following by means of examples.

EXAMPLE 1 a) Preparation of a lipid film and transfer of same into a crude mixture consisting of (phospho)lipid(s) and aqueous medium Preparation of a lipid solution by dissolving 5.96 grams of hydrogenated soy phosphatidyl choline together with 3.04 grams of cholesterol (according to a molar ratio of the two membrane-forming amphiphiles of 1:1) in chloroform.

Subsequent complete removal of the chloroform by evaporation using a rotary evaporator at temperatures of about 40 to 60° C. and a reduced pressure between 400 to 20 hPa. Upon addition of 21 ml of an approximately 0.1 millimolar aqueous solution of the hydrophilic low molecular-weight marker 5,6-carboxyfluorescein in 40 millimolar phosphate buffer (pH 7.4), the lipid film is dispersed by manual shaking at an elevated temperature (about 60 to 70° C.).

b) High-pressure Homogenization

The crude mixture obtained from the procedure described under a) is subjected ten times to a high-pressure homogenization using an APV Gaulin Micron Lab 40 high-pressure homogenizer at pressures of 70 MPa. The crude mixture or educt, the homogenizer and the product are maintained and tempered at temperatures above 60° C.

c) Transfer of the Preparation into a Freely Flowing Liposome Dispersion

By a stepwise adding of aqueous medium in portions of 10% of the volume of the preparation as obtained in step b) and mechanical mixing, for example, by manual shaking or with a Vortex vibrating mixer, the three-dimensional gel assembly is dispersed and the preformed liposomes are released.

d) Separation and Quantitative Determination of Content of Liposomally Entrapped 5,6-carboxyfluorescein and of the Unentrapped Marker for Determining the Encapsulation and Entrapment Efficiency The separation of the liposomesis carried out by size exclusion chromatography or gel permeation chromatography on a column filled with preswollen Sephadex G25 (Pharmacia) and elution using a 40 millimolar phosphate buffer (pH 7.4). The 5,6-carboxyfluorescein amount present in the liposome fractions and the fraction, which contains the free 5,6-carboxyfluorescein, is quantified fluorimetrically at an excitation wavelength of about 486 nm and an emission wavelength of about 516 nm. A possible turbidity, caused by the liposomes and which hampers the analysis, is removed by the addition of a 25% solution of bile salts. A quantitative determination is made against a calibration series of diluted solutions of 5,6-carboxyfluorescein in 40 millimolar phosphate buffer (pH 7.4) of a known content. The thereby determined relative proportions of liposomally entrapped 5,6-carboxyfluorecein (entrapment efficiency) are compared to the total marker contained in the liposome dispersion and the encapsulation efficiency obtained in this way amounts to about 40%.

e) Electron Microscopic Visualization and Size Analysis of the Liposomes

Figure 2:
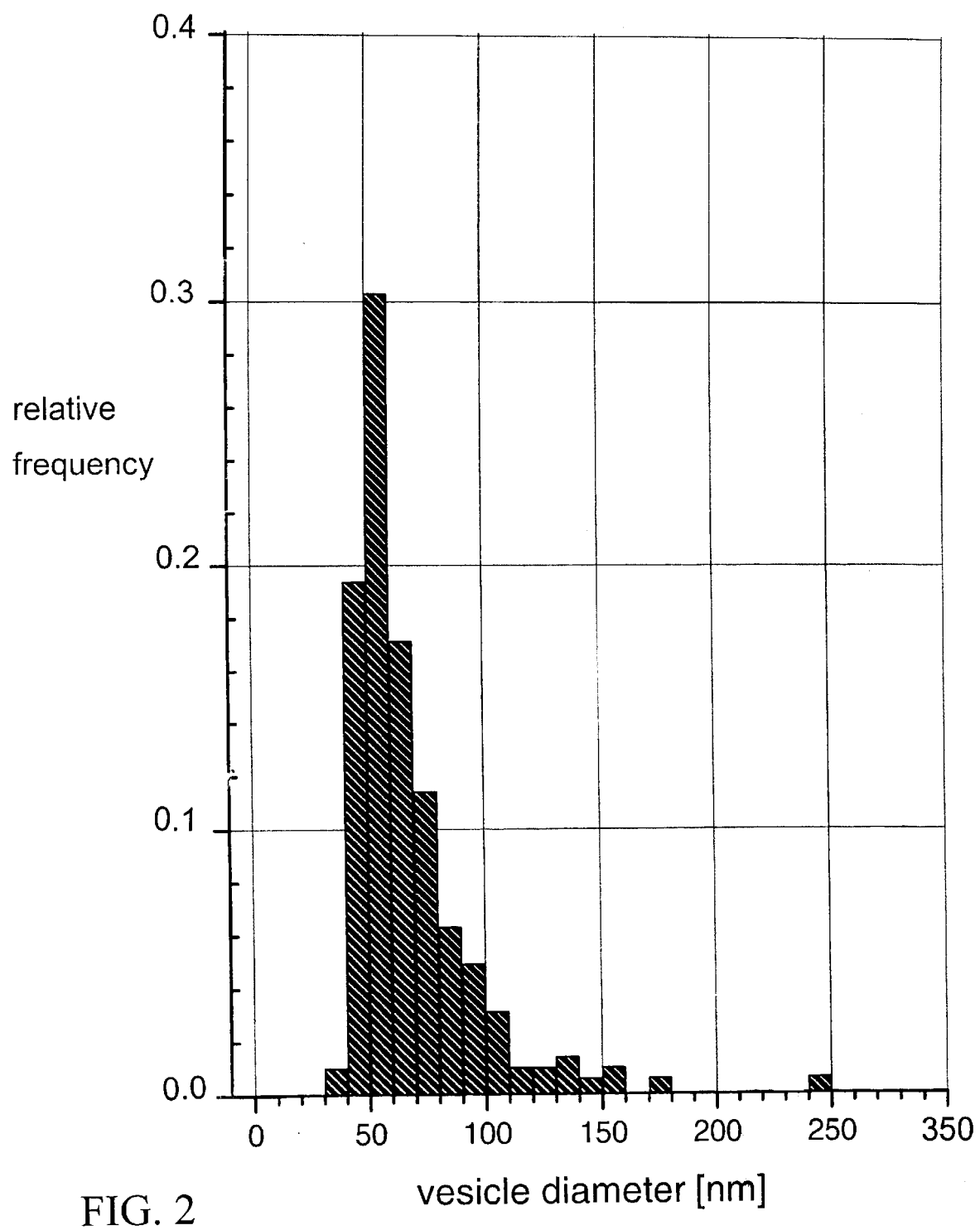
FIG. 2 is a view of a histogram of the size distribution of the liposome diameter—Hydrated soy phosphatidyl choline and cholesterol, dispersion 30% (m/m), homogenized 10×70 MPa, visualized with Cryo-EM.

The illustration shown in FIG. 1 gives a micrograph picture of the liposomes as obtained in step c) which has been made by Cryo-electron microscopy. It is obvious from FIG. 1 that the liposomes are present as separate particles and that the overwhelming majority of the liposomes are of small and uniform size and unilamellar. The result of a size analysis of over 400 of the depicted vesicles or liposomes is given in the histogram shown in FIG. 2.

EXAMPLE 2 a) High-pressure Homogenization 12 grams of soy phosphatidyl choline and 18 milliliters of an approximately 0.1 millimolar aqueous solution of the low-molecular weight hydrophilic marker 5,6-carboxyfluorescein in a 40 millimolar phosphate buffer (pH 7.4) are mixed by manual shaking.

The obtained mixture is subjected ten times to the high-pressure homogenization, employing an APV Gaulin Micron Lab 40 high-pressure homogenizer, at pressures of 70 MPa.

b) Freeze-thaw Cycles

The gel-like preparation obtained in step a) is frozen at temperatures of −10° C. or below and subsequently thawed at temperatures of 60° C. or above. This freeze/thaw cycle is carried out successively for a total of three times.

c) Transfer of the Preparation into a Freely Flowing Liposome Dispersion

By a stepwise adding of aqueous medium in portions of 10% of the volume of the preparation as obtained in step b) and mechanical mixing, for example, by manual shaking or with a Vortex vibrating mixer, the three-dimensional gel assembly is dispersed and the preformed liposomes are released.

d) Separation and Quantitative Determination of Content of Liposomally Entrapped 5,6-carboxyfluorescein and of the Unentrapped Marker for Determining the Encapsulation and Entrapment Efficiency The separation of the liposomesis carried out by size exclusion chromatography or gel permeation chromatography on a column filled with preswollen Sephadex G25 (Pharmacia) and elution using a 40 millimolar phosphate buffer (pH 7.4). The 5,6-carboxyfluorescein amount present in the liposome fractions and the fraction, which contains the free 5,6-carboxyfluorescein, is quantified fluorimetrically at an excitation wavelength of about 486 nm and an emission wavelength of about 516 nm. A possible turbidity, caused by the liposomes and which hampers the analysis, is removed by the addition of a 25% solution of bile salts. A quantitative determination is made against a calibration series of diluted solutions of 5,6-carboxyfluorescein in 40 millimolar phosphate buffer (pH 7.4) of a known content.

The thus determined relative proportions of the liposomally entrapped 5,6-carboxyfluorescein (entrapment efficiency) relative to the total marker contained in the liposome dispersion amounts to about 80% (encapsulation efficiency).

EXAMPLE 3 a) Preparation of a Lipid Film and Transfer of the Same into a Crude Mixture Consisting of (Phospho)lipid(s) and Aqueous Medium Preparation of a lipid solution by dissolving 4.42 grams of soy phosphatidyl choline together with 0.535 grams of cholesterol (corresponding to a molar ratio of the two membrane-forming agents of 1:0.25) in chloroform. Subsequently, complete removal of the chloroform by evaporation using a rotary evaporator at temperatures of about 40° to 60° C. and reduced pressure between 400 and 20 hPa. Dispersion of the lipid film upon addition of 25 milliliters of an approximately 0.68 millimolar aqueous solution of the low-molecular weight hydrophilic cytostatic agent carboplatin.

b) High-pressure Homogenization

The mixture obtained from step a) is subjected ten times to the high-pressure homogenization, employing an APV Gaulin Micron Lab 40 high-pressure homogenizer, at pressures of 70 MPa.

c) Freeze-thaw Cycles

The gel-like preparation obtained in step a) is frozen at temperatures of −10° C. or below and subsequently thawed at temperatures of 60° C. or above. This freeze/thaw cycle is carried out successively for a total of three times.

d) Transfer of the Preparation into a Freely Flowing Liposome Dispersion

By a stepwise adding of aqueous medium in portions of 10% of the volume of the preparation as obtained in step b) and mechanical mixing, for example, by manual shaking or with a Vortex vibrating mixer, the three-dimensional gel assembly is dispersed and the preformed liposomes are released.

e) Separation and Analytical Determination of Content of the Liposomally Entrapped Carboplatin The separation of the liposomes, prepared as described under 3b, from unentrapped material is carried out by size exclusion chromatography or gel permeation chromatography on a column filled with preswollen Sephadex G25 and elution with isotonic phosphate buffer (pH 7.4).

Liposomes which had been prepared according to Example 3 c) are mixed three times with in each case 100 ml of isotonic phosphate buffer (pH 7.4) and centrifuged for 30 minutes at 14,000 rpm, the pellet is resuspended. This procedure is repeated twice.

The quantitative determination of the proportion of entrapped carboplatin is done via high-pressure liquid chromatography (HPLC) analysis (I Fichtner, R. Reszka, M. Schutt, M. Rudolph, M. Lemm, J. Richter, I. Berger, Carboplatin-Liposomes as Activators of Hematopoiesis, Oncology Research 5: 65–74, 1993).

The encapsulation and entrapment efficiency obtained this way is approximately 40% (of total carboplatin employed for the preparation).

EXAMPLE 4

4.4 grams of soy phosphatidyl choline and 20 milliliters of an approximately 0.94 millimolar aqueous solution of the low-molecular weight hydrophilic cytostatic agent are mixed by manual shaking. The obtained mixture is processed ten times by high-pressure homogenization, employing an APV Gaulin Micron Lab 40 high-pressure homogenizer, at pressures of 70 MPa.

b) Freeze-thaw Cycles

The gel-like preparation obtained in step a) is frozen at temperatures of −10° C. or below and subsequently thawed at temperatures of 60° C. or above. This freeze/thaw cycle is carried out successively for a total of three times.

c) Transfer of the Preparation into a Freely Flowing Liposome Dispersion

By a stepwise adding of aqueous medium in portions of 10% of the volume of the preparation as obtained in step b) and mechanical mixing, for example, by manual shaking or with a Vortex vibrating mixer, the three-dimensional gel assembly is dispersed and the preformed liposomes are released.

d) Separation and Analytical Determination of Content of the Liposomally Entrapped Carboplatin The separation of the liposomes, prepared as described under Example 3b), from unentrapped material is carried out by size exclusion chromatography or gel permeation chromatography on a column filled with preswollen Sephadex G25 and elution with isotonic phosphate buffer (pH 7.4).

Liposomes which had been prepared according to Example 3c) are mixed three times with in each case 100 ml of isotonic phosphate buffer (pH 7.4) and centrifuged for 30 minutes at 14,000 rpm, the pellet is resuspended. This procedure is repeated twice.

The quantitative determination of the proportion of entrapped carboplatin is done via high-pressure liquid chromatography (HPLC) analysis (I Fichtner, R. Reszka, M. Schutt, M. Rudolph, M. Lemm, J. Richter, I. Berger, Carboplatin-Liposomes as Activators of Hematopoiesis, Oncology Research 5: 65–74, 1993).

The encapsulation and entrapment efficiency obtained this way is about 44% (of total carboplatin employed for the preparation).

EXAMPLE 5

Preparation

Preparation of highly concentrated phospholipid dispersions has been done by using the one-step homogenization technique as described earlier, M. Brandl, D. Bachmann, M. Drechsler, and K. H. Bauer, 1990, Liposome preparation by a new high-pressure homogenizer Gavlin Macron Lab 40 Drug Dev. Ind. Pharm. 16, 2167–2192, for liposome preparation purposes. In brief, dry, powdered phosphatidyl choline was mixed with buffer solution (isotonic phosphate buffer pH 7.4) or calcein solution and fed into a APV Micron Lab 40 high-pressure homogenizer and homogenized ten times at pressure of 70 MPa. These conditions had been found ideal in previous studies for liposome preparation, M. Brandl, D. Bachmann, M. Drechsler, and K. H. Bauer, 1993, Liposome Preparation using High-pressure Homogenizers, in G. Gregoriadis (Ed.) Liposome Technology 2nd edition, Vol. 1, pp. 49–65, CRC, Boca Raton.

Electron Microscopy

Small samples were mounted on a gold specimen holder (Balzers) and quick-frozen in liquid ethane cooled to 77–100 K. Upon fracturing using a Balzers BAF 301 device, the surface was etched for 30 s at 173 K. Subsequently, the etched surface was vacuum deposited with platinum/carbon (2 nm) and carbon (30 nm) at an angle of 40–450. The obtained replica was floated off and cleaned in an ethanol/chloroform or ethanol/water mixture. Visualization was performed on a Philips EM 400 transmission electron microscope (80 kV).

Release Tests

The in-vitro release testing was performed using a flow through apparatus (homemade release cell as described in detail in M. Brandl and R. Reszka, 1995, Preparation and characterization of phospholipid membrane gels as depot formulations for potential use as implants, Proc. Intern. Symp. Control. Rel. Bioac Mater. 22, 472–473. The lower cavity of the cell was filled with approximately 1 g of a paste containing calcein as hydrophilic marker, whereas the upper cavity was continuously rinsed with isotonic phosphate buffer pH 7.4 at a flow rate of 10 ml/h. The two compartments were not separated by a membrane. In the collected fractions, the hydrophilic marker was quantified either directly or when they were opalescent or turbid after size exclusion chromatographic separation using Sephadex G50 medium gel (Pharmacia) in the sub-fractions assigned to as free and liposome-bound marker.

Results a) Structure Analysis

Figure 3:
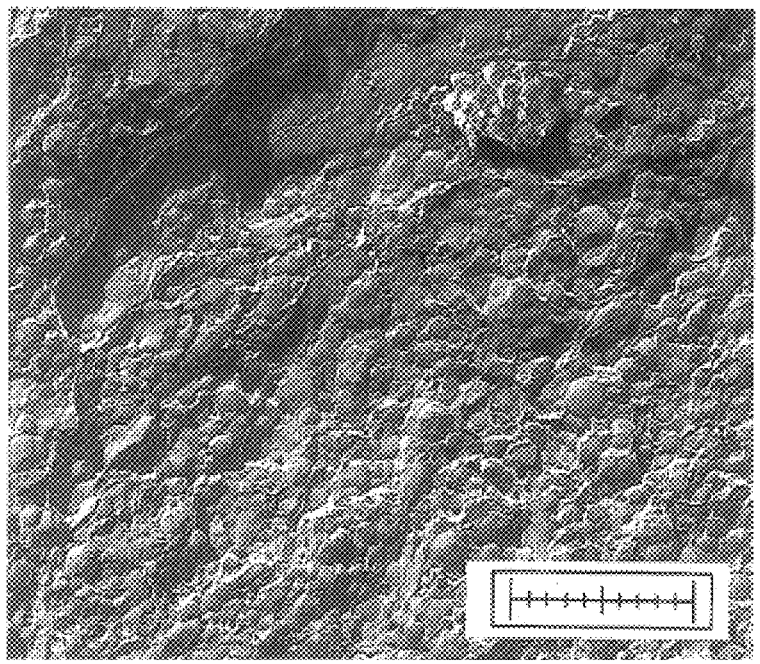
FIG. 3 is a view of a FF-TEM micrograph of 60% soy phosphatidyl choline dispersion in buffer. Sample was LI prepared by high-pressure homogenization at 10×70 MPa. Matrix is predominantly composed of small uniform vesicles and staples of lamellae with embedded large multilamellar vesicles: bar is 1 $\mu$m in total.

An example of a freeze-fracture electron micrograph of a semisolid dispersion which contained 60% of soy phosphatidyl choline PC is given in FIG. 3. Here, as with all semisolid matrices of lower lipid content, one predominant structural element was observed: vesicles. With matrices of lipid concentrations of 50% and above, these vesicles showed great variability in size as well as lamellarity; besides small unilamellar vesicles (SUVs), large multilamellar vesicles (MLVs) and planar staples of bilayers which can also be addressed as flattened MLVs were found. In contrast, at lower lipid concentrations, the preparations seem to consist exclusively of a matrix of densely packed liposomes, which are quite small, below 100 nm in diameter, uniform and unilamellar. We have thus been using the expression "networks of liposomes" although a network besides a coherent structure (here of liposomes) usually contains a liquid phase in between which cannot be identified from our micrographs.

b) In vitro Release Studies

Figure 4:
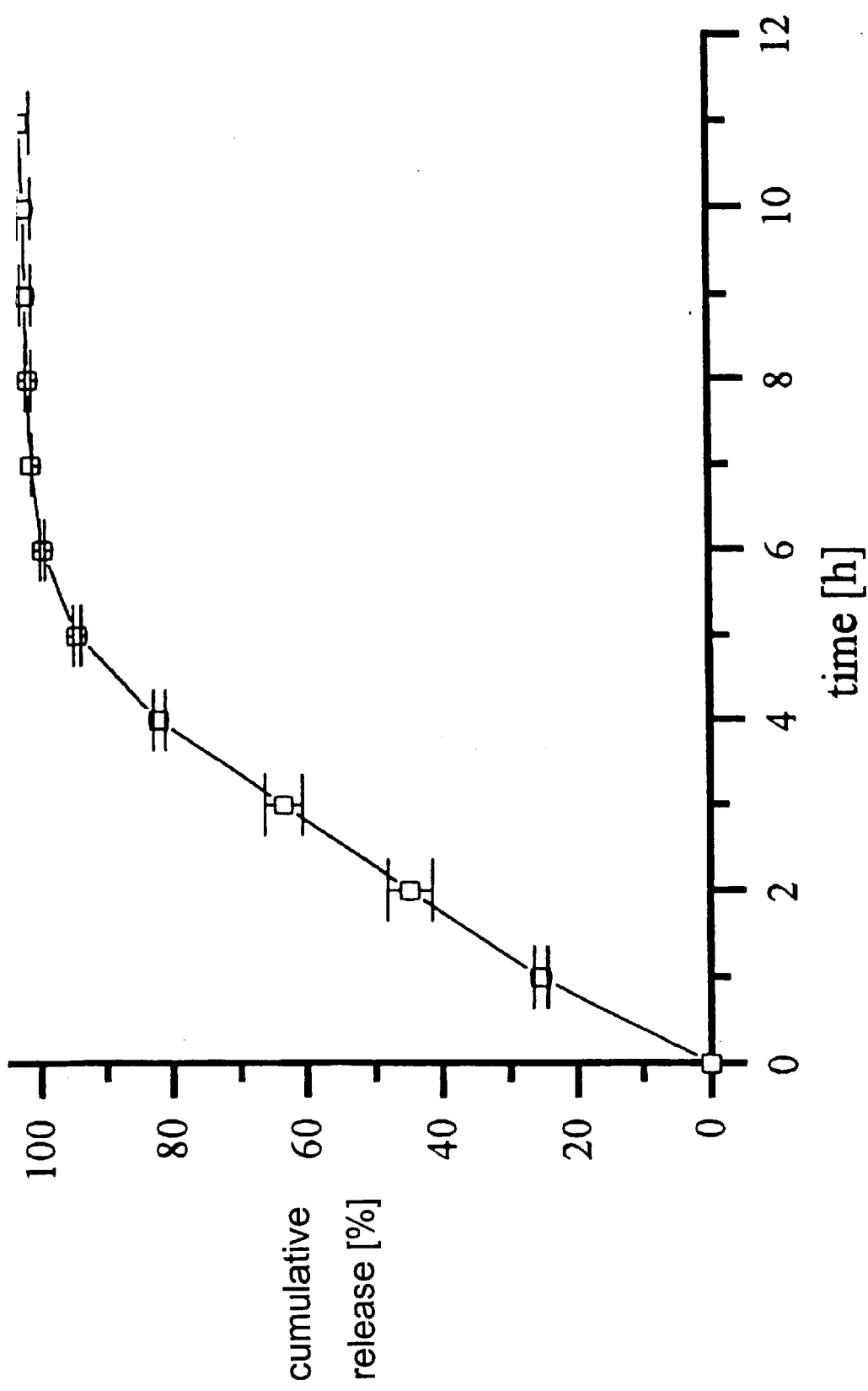
FIG. 4 is a view of a diagram showing cumulative release of calcein from 40% egg phosphatidyl choline dispersion. Cumulative amount of calcein released in percent of total calcein in the depot plotted versus time. Each data point represents mean and standard deviation of three experiments.
Figure 5:
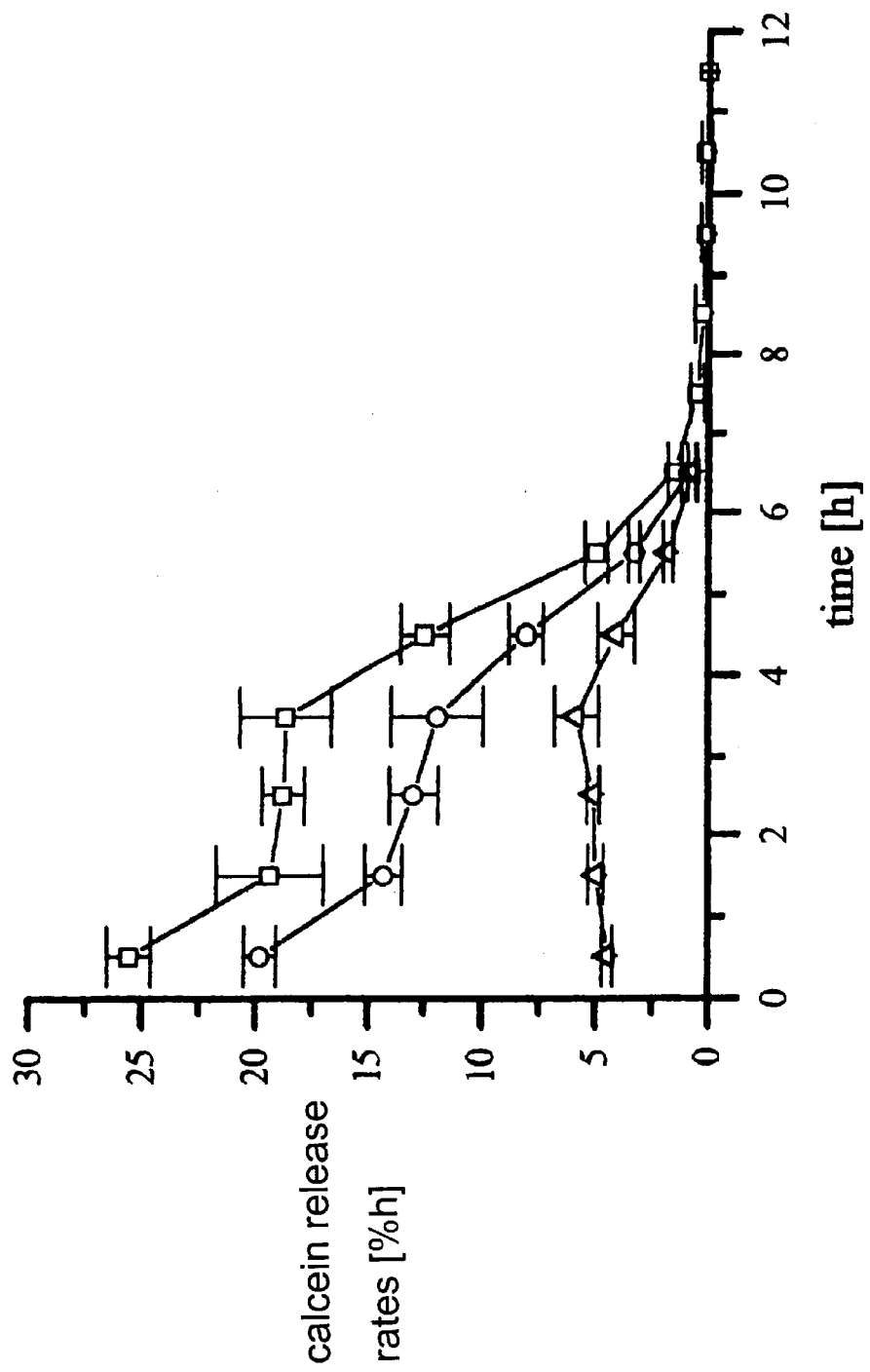
FIG. 5 is a view of a diagram showing release rates of calcein from 40% egg phosphatidyl choline dispersion. Release rates of free, liposomal and total calcein plotted versus time. Each data point represents mean and standard deviation of three experiments.

The multi-vesicular semisolid matrices were found to retain incorporated hydrophilic markers such as carboxyfluorescein or calcein, M. Brandl and R. Reszka, 1995, Preparation and characterization of phospholipid membrane gels as depot formulations for potential use as implants, Proc. Intern. Symp. Control. Rel. Bioac Mater. 22, 472–473; M. Brandl, C. Tardi, M. Menzel, and R. Reszka, 1995, Highly concentrated phospholipid dispersions: preparation by high pressure homogenization and analysis of drug release. Proceedings 4th Liposome Res. Days. Freiburg PS1, and release them in a controlled manner when coming in contact with excess aqueous medium. A typical cumulative release pattern for sustained release of calcein from a 40% egg phosphatidyl choline PC dispersion is shown in FIG. 4. By size exclusion chromatography, the released medium could be further fractionated: markers were found to be released in free as well as in liposome-entrapped form (FIG. 5). In further studies, we tried to elucidate whether the release kinetics of the incorporated marker can be influenced by the concentration of phosphatidyl choline PC in the matrix. The overall tendency observed was a decrease of release rate with increasing lipid concentration for lipid concentrations between 30 and 60% (m/m). When comparing lipid concentrations of 40 and 50% (m/m), however, a dramatic change was found. Whereas 40% (m/m) matrices showed mean release rates of about 15% of total incorporated marker per hour and durations of about 6 h until 100% release was achieved, the 50% (m/m) matrices released only 2% per hour in mean and release continued for more than 48 h. The fraction of the marker released in liposome-entrapped form was also much smaller with the more concentrated matrix. None of the matrix was left in the release cell after the end of marker release from the 40% (m/m) preparation. In contrast with 50% (m/m) matrices the cell still contained a remainder of the lipid matrix which had been depleted of all marker.

DISCUSSION

From electron microscopical evaluation it is seen that there occur structural changes of the matrices at a critical lipid concentration between 40 and 50% (m/m). Matrices consisting of 40% or less of lipid showed structures of densely packed SUVs throughout. In contrast, matrices of lipid concentrations of 50% and above showed various structural elements besides SUVs, large MLVs, and deformed MLVs were also found. The three-dimensional liposomal networks below the critical concentration solely consist of SUVs and thus fully erode by continuous "budding off" of intact liposomes. Above this critical concentration, on the other hand, only a proportion of SUVs is embedded in less defined structures which do not erode easily. The marker in this case is released quite exclusively via diffusion. In conclusion, raising the lipid concentration does not only affect the release rate but, beyond a certain border, also causes a change in release mechanism.

It will be understood that each of the steps, conditions, and reagents described above, or two or more together, may also find a useful application in other types of reactions, gas processing procedures, and products differing from the types described above.

While the invention has been illustrated and described as embodied in the context of a method for production of liquefied gases, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is:

1. A liposome preparation consisting essentially of a vesicular lipid gel which is formed of liposomes made of a phospholipid, water, at least 20% by weight of an active substance entrapped within the liposomes, and optionally an electrolyte, the gel having a lipid concentration of about 40 to about 60% by weight with respect to the preparation, wherein about 95% or more by weight of the liposomes of said preparation are unilamellar and have a diameter of about 10 to about 300 nm within a 100 nm range, the preparation being formed by subjecting the liposomes, water, active substance and optionally the electrolyte, to a high-pressure homogenization under pressure of from about 5–160 MPa.

2. The liposome preparation of claim 1, wherein the lipid concentration is about 40 to about 50%.

3. The liposome preparation of claim 1, wherein at least about 40% by weight of the active substance is entrapped within the liposomes.

4. A liposome preparation consisting essentially of a vesicular lipid gel which is formed of liposomes made of a phospholipid and a cholesterol, water, at least 20% by weight of an active substance entrapped within the liposomes, and optionally an electrolyte, the gel having a lipid concentration of about 40 to about 60% by weight with respect to the preparation, wherein about 95% or more by weight of the liposomes of said preparation are unilamellar and have a diameter of about 10 to about 300 nm within a 100 nm range, the preparation being formed by subjecting the liposomes, water, active substance and optionally the electrolyte, to a high-pressure homogenization under pressure of from about 5–160 MPa.

5. The liposome preparation of claim 4, wherein the lipid concentration is about 40 to about 50%.

6. The liposome preparation of claim 4, wherein at least about 40% by weight of the active substance is entrapped within the liposomes.

* * * * *

UNITED STATES PATENT AND TRADEMARK OFFICE
CERTIFICATE OF CORRECTION

| | | |
|---|---|---|
| PATENT NO. | : 6,399,094 B1 | Page 1 of 1 |
| DATED | : June 4, 2002 | |
| INVENTOR(S) | : Martin Brandl, Dieter Bachmann, Regine Rezka and Markus Dreschsler | |

It is certified that error appears in the above-identified patent and that said Letters Patent is hereby corrected as shown below:

<u>Title page,</u>
Insert the following:
-- [30]    Foreign Application Priority Data
   Aug. 20, 1994  (DE) ..................... P 44 30 592.3 --

Signed and Sealed this

Twenty-fourth Day of December, 2002

JAMES E. ROGAN
*Director of the United States Patent and Trademark Office*